United States Patent [19]
Wright et al.

[11] 4,064,134
[45] Dec. 20, 1977

[54] ETHYL-3-(3-AMINO-2-PYRIDYL)CARBAZATE HYDROCHLORIDE

[75] Inventors: George C. Wright, Norwich; James L. Butterfield, New Berlin, both of N.Y.

[73] Assignee: Morton-Norwich Products, Inc., Norwich, N.Y.

[21] Appl. No.: 716,215

[22] Filed: Aug. 20, 1976

[51] Int. Cl.$^2$ .................... C07D 213/77; C07C 85/11; A61K 31/44

[52] U.S. Cl. .............................. 260/295 CA; 260/580; 424/263

[58] Field of Search .......................... 260/295 CA, 580

[56] References Cited
U.S. PATENT DOCUMENTS 3,278,603  10/1966  Cooke ................................. 260/580

Primary Examiner—Donald G. Daus
Assistant Examiner—Lisa Jones
Attorney, Agent, or Firm—Anthony J. Franze

[57] ABSTRACT

The title compound is an antihypertensive agent.

1 Claim, No Drawings

ETHYL-3-(3-AMINO-2-PYRIDYL)CARBAZATE HYDROCHLORIDE

This invention is concerned with the chemical compound ethyl 3-(3- amino-2-pyridyl)carbazate hydrochloride having pharmacological activity. In a particular aspect of its pharmacological activity it has been found to exert a potent antihypertensive effect. When administered intraperitoneally at a dose of 50 mg/kg or perorally at a dose of 10 mg/kg to unanesthetized spontaneously hypertensive rats a salutary reduction in blood pressure is elecited.

The compound of this invention is readily formulated in conventional pharmaceutical dosage forms such as tablets, elixirs, suspensions, capsules, solutions, dragees and the like employing excipients, adjuvants and additives known to the apothecary art and with which there is no incompatibility.

In order that this invention may be readily available to and understood by those skilled in the art the currently preferred method for making it is briefly described:

Ethyl 3-(3-Amino-2-pyridyl)carbazate Hydrochloride

A. Ethyl 3-(3-Nitro-2-pyridyl)carbazate Hydrochloride

A 24 g (0.15 mole) portion of 2-chloro-3-nitropyridine in 153 ml of phenol at 45°–50° was treated portionwise with 20.5 g (0.20 mole) of ethyl carbazate, keeping the temperature below 60°, using rapid mechanical stirring. The reaction mixture was heated on a steam bath for 5 hr, cooled to 45 –55°, and poured into 750 ml of anhydrous ether, using rapid hand stirring. A light orange solid was collected, washing with 400 ml of anhydrous ether, m.p. 142°–152° dec. Yield: 34 g (85%).

B. Ethyl 3-(3-Amino-2-pyridyl)carbazate Hydrochloride

The ethyl 3-(3-nitro-2-pyridyl)carbazate hydrochloride 34 g (0.13 mole) was slurried in 300 ml of isopropanol and treated with 4.4 g of 5% pd/C (50% $H_2O$) in 40 ml of isopropanol. The reaction mixture was subjected to hydrogenation at 50 psig. A 24 psig drop at 27°0 was observed (theory 30 No. at 27°), and the mixture was cooled overnight. The crystalline product was collected along with the catalyst. The product was taken up in 300 ml of hot methanol, the catalyst filtered, and the product precipitated from the filtrate, m.p. 217°–219° dec. Yield: 11 g (37%).

Analysis Calcd. $C_8H_{12}N_4O_2$. HCL: C, 41.29; H, 5.63; N, 24.08; Found: C, 41.38; H, 5.60 ; N, 23.73

What is claimed is:

1. Ethyl 3-(3-amino-2-pyridyl)carbazate hydrochloride.